United States Patent
Chun et al.

(10) Patent No.: US 8,352,060 B2
(45) Date of Patent: Jan. 8, 2013

(54) COMPUTER-AIDED FABRICATION OF A REMOVABLE DENTAL PROSTHESIS

(75) Inventors: James Jiwen Chun, Raleigh, NC (US); Angela Soyoung Chun, Raleigh, NC (US); Andrew Youngho Chun, Raleigh, NC (US); Jennifer Miseong Chun, Raleigh, NC (US)

(73) Assignee: Hankookin, LLC., Raleigh, NC (US)

( * ) Notice: Subject to any disclaimer, the term of this patent is extended or adjusted under 35 U.S.C. 154(b) by 172 days.

(21) Appl. No.: 12/774,222

(22) Filed: May 5, 2010

(65) Prior Publication Data

US 2011/0276159 A1 Nov. 10, 2011

(51) Int. Cl.
*G06F 19/00* (2011.01)

(52) U.S. Cl. ............. 700/118; 700/96; 700/98; 700/159

(58) Field of Classification Search ............... 700/96–98, 700/159, 163–164, 117–120
See application file for complete search history.

(56) References Cited

U.S. PATENT DOCUMENTS

| | | | |
|---|---|---|---|
| 6,152,731 A * | 11/2000 | Jordan et al. ............... | 433/69 |
| 2004/0197728 A1 | 10/2004 | Abolfathi et al. | |
| 2005/0070782 A1 | 3/2005 | Brodkin | |
| 2005/0089822 A1 | 4/2005 | Geng | |
| 2007/0165022 A1* | 7/2007 | Peleg et al. ............... | 345/419 |
| 2007/0207437 A1 | 9/2007 | Sachdeva et al. | |
| 2008/0090207 A1 | 4/2008 | Rubbert | |
| 2009/0081618 A1* | 3/2009 | LaMar ............... | 433/218 |
| 2009/0092948 A1 | 4/2009 | Gantes | |
| 2009/0316966 A1 | 12/2009 | Marshall et al. | |
| 2010/0082148 A1* | 4/2010 | Cinader, Jr. ............... | 700/120 |
| 2010/0291505 A1* | 11/2010 | Rawley et al. ............... | 433/72 |

FOREIGN PATENT DOCUMENTS

| | | | |
|---|---|---|---|
| WO | WO2008128700 | * | 10/2008 |
| WO | WO2010002058 | * | 1/2010 |
| WO | WO2010023665 | * | 3/2010 |

OTHER PUBLICATIONS

Rodrigues et al. "A Biomechanical Model of the Upper Airways for Simulating Laryngoscopy", Computer Methods in Biomechanics and Biomedical Engineering, vol. 4, pp. 127-148, 2001.*

* cited by examiner

*Primary Examiner* — Carlos Ortiz Rodriguez
(74) *Attorney, Agent, or Firm* — Ash Tankha; Lipton, Weinberger & Husick

(57) ABSTRACT

A method and system for fabricating a dental prosthesis are provided. High resolution digital scanned images of a patient's oral structures are acquired. Three dimensional (3D) cone beam X-ray images of hard and soft oral tissues are acquired. The scanned images are integrated with the 3D cone beam X-ray images in a 3D space to obtain combined three dimensional images of the oral structures. The occlusal relationship between upper and lower oral structures are digitally simulated using the combined three dimensional images. The dental prosthesis is digitally modeled for planning intra-oral positioning and structure of the dental prosthesis. The digital dental prosthesis model is refined based on simulated force tests performed for assessing interference and retention of the digital dental prosthesis model. A prospective dental prosthesis model is created based on the refined digital dental prosthesis model. The dental prosthesis is fabricated based on a verified prospective dental prosthesis model.

26 Claims, 13 Drawing Sheets

COMPUTER-AIDED FABRICATION OF A REMOVABLE DENTAL PROSTHESIS

BACKGROUND

Dental prostheses are prosthetic appliances that replace missing teeth to aid mastication and improve facial esthetics, phonetics, and self esteem. Removable dental prostheses include dentures, partial dentures, and detachable fixed prostheses. The traditional methods of fabricating removable prostheses rely on alginate or silicone impressions of bone, soft tissue structures, and the dentition of a patient. These methods usually require multiple patient visits to obtain a clinically acceptable impression. The impressions are poured with dental stone to obtain model casts or replicas of the upper and lower jaws. Model casts or casts are plaster replicas of dental structures obtained from impressions of the dental structures.

A proper clinical step in prosthodontics requires a face bow transfer that records the position of the upper teeth in relation to the maxillary jaw. In addition to the face bow transfer records, the bite registration of the upper jaw and the lower jaw while the mandibular condyle is placed in functional positions such as the centric relation is also taken. Due to the involvement of the masticular muscle groups, there have been controversies over the definition and method of obtaining accurate occlusion data.

The face bow transfer and bite registration are then used to mount the upper and lower jaw casts onto a semi-adjustable mechanical articulator that simulates the mandibular jaw motion. The semi-adjustable dental articulator has a fixed or semi-adjustable condyle portion, a fixed lower jaw portion, with a simplified limited operation of jaw motion. These mounted casts of the upper jaw and the lower jaw are sent to dental labs, where prosthetic teeth are set in wax form for a patient's try-in. At the try-in appointment, the wax prosthesis is examined for esthetics, occlusion, and speech. Esthetics usually requires a proper smile profile, for example, with the teeth showing when smiling, and around 1 mm-2 mm of the teeth showing at the resting position of the upper lip. Occlusion requires proper contacts between the upper teeth and low teeth. Speech requires a proper seal between the upper teeth and the lower lips.

After a number of try-ins, the final wax form with properly set teeth is returned to the dental labs for processing. While the teeth are held in place by investing materials, the wax portion is replaced by pink tissue-colored acrylic materials and polymerized under high pressure and temperature. The polymerized products are then trimmed and polished to develop the finished prostheses. The entire process typically takes one to two months. Moreover, these prostheses require extensive adjustments and multiple additional visits, and also do not guarantee patient satisfaction.

While every step in the dental clinic and the dental lab requires tedious and precision-driven labor, human errors are inevitable. Furthermore, there are many inherent sources of errors that are difficult to control, for example, soft tissue deformation during impression, limitations of the semi-adjustable articulator, controversies over proper form of occlusion, and shrinkage of acrylic material during polymerization.

A major problem involving removable prosthesis is the retention of the prosthesis. Although the acrylic material adapts to the shape of the plaster cast model initially, the acrylic base shrinks and deforms during the polymerization process, thereby losing its precise seal to the plaster model and the soft tissue. If the base of the prosthesis does not seal tightly to the soft oral tissues, food particles and air can seep into the space under the prosthesis and make it less retentive. On the other hand, over retention due to lack of precision in metal framed partial dentures is also a problem. Over retention not only causes pain and discomfort, but also damages the anchoring teeth in the long term. Due to the lack of technology to precisely shape the base or anchor area of the prosthesis, current methods mostly rely on multiple clinical adjustments by the dentist using pressure-indicating paste, which still does not warrant a tight seal or fit to the tissue surfaces. Dentists often spend significant time adjusting the base of the prosthesis and patients are generally unhappy with the outcome. Another problem is improper occlusion due to inaccurate face bow transfer or the absence of a face bow transfer. This results in unbalanced occlusion interference, improper teeth alignment, or insufficient occlusion space, which further reduce the retention. As a result of these unresolved problems, the service of removable prostheses is currently under-valued and under-served in the dental industry.

Hence, there is a long felt but unresolved need for a computer-aided method and system for designing and fabricating a highly retentive, functional, and esthetic removable dental prosthesis for a patient.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The computer-aided method and system disclosed herein addresses the above stated need for designing and fabricating a highly retentive, functional, and esthetic removable dental prosthesis for a patient. One or more three dimensional high resolution digital scanned images of one or more oral structures of the patient are acquired using one or more digital image scanning devices. One or more three dimensional cone beam X-ray images of hard oral tissues and soft oral tissues of the patient are acquired using a cone beam X-ray image device. The high resolution digital scanned images of the oral structures are integrated with the three dimensional cone beam X-ray images of the hard oral tissues and the soft oral tissues of the patient in a three dimensional space to obtain one or more combined three dimensional images of the oral structures of the patient. The combined three dimensional images render low resolution images of upper jaw bones and lower jaw bones, roots of teeth, and temporomandibular joint complex, and high resolution images of coronal portion of the teeth and the soft oral tissues that potentially interface with the dental prosthesis. An occlusal relationship between upper oral structures and lower oral structures are digitally simulated using the combined three dimensional images for digitally articulating the upper oral structures and the lower oral structures. The occlusal relationship between the upper oral structures and the lower oral structures is digitally simulated at different functional condylar positions for digitally reproducing bite registration, centric occlusion, and centric relation.

The dental prosthesis is digitally modeled based on the digitally articulated upper oral structures and lower oral structures to generate a digital dental prosthesis model for planning intra-oral positioning and structure of the dental prosthesis. The intra-oral positioning and the structure of the dental prosthesis are planned for achieving optimal occlusion, retention, smile profile, and for meeting phonetic requirements of the dental prosthesis. The dental prosthesis is digitally modeled by establishing a preliminary digital model of the dental prosthesis using pre-scanned digital models stored in an image database of dental prosthesis design. The image database comprises pre-stored digital models of different dental prostheses previously scanned or modeled based on multiple forms of dentition and upper and lower jaw configuration. The preliminary digital model of the dental prosthesis is established by matching the pre-scanned digital models with jaw morphology and configuration of the patient obtained by characterizing arch form and size of upper and lower jaws, ridge height and form, and inter-jaw space and relation. The preliminary digital model of the dental prosthesis is established by simulating and parameterizing elastic response of the soft oral tissues, occlusion force interaction between upper teeth and lower teeth, condylar guidance, lifting force of upper lip and lower lip, tongue motion, and oral muscles during primary motions of the oral structures of the patient.

The digital dental prosthesis model is refined based on simulated force tests performed for assessing interference and retention of the digital dental prosthesis model. The simulated force tests are performed for reducing interference and enhancing retention of the digital dental prosthesis model by simulating predetermined motions of the oral structures. The digital dental prosthesis model is refined by modifying the configurations, for example, position, alignment and height of teeth of the digital dental prosthesis model.

A prospective dental prosthesis model is created based on the refined digital dental prosthesis model. The prospective dental prosthesis model is tested for verifying predetermined functions, for example, retention of the prospective dental prosthesis model, esthetics of the prospective dental prosthesis model, and occlusion and phonetics of the prospective dental prosthesis model. Testing the prospective dental prosthesis model comprises analyzing and incorporating modifications into the refined digital dental prosthesis model, creating a modified prospective dental prosthesis model, and verifying the modified prospective dental prosthesis model. The dental prosthesis is fabricated based on the tested and verified prospective dental prosthesis model. The designed and fabricated dental prosthesis is a removable complete denture dental prosthesis, a removable partial denture dental prosthesis, or a detachable fixed dental prosthesis anchored on natural oral structures or implanted oral structures.

An acrylic base of the dental prosthesis is digitally modeled based on the simulated force tests. The acrylic base is configured for establishing a complete peripheral air tight seal with the hard oral tissues and the soft oral tissues to achieve suction based retention of the dental prosthesis.

The fabricated dental prosthesis is subjected to a milling process for gross cutting and fine detailing to obtain a finished product. A three dimensional image, spatial location, and orientation of the fabricated dental prosthesis are acquired. An automated milling sequence is configured based on a comparison between the acquired three dimensional image of the fabricated dental prosthesis and the refined digital dental prosthesis model. The fabricated dental prosthesis is subjected to milling based on the milling sequence for gross cutting and fine detailing of the fabricated dental prosthesis.

In an embodiment, the dental prosthesis is fabricated by casting metal into a preformed space of the prospective dental prosthesis model. In another embodiment, the dental prosthesis is fabricated by molding acrylic material into a preformed space of the prospective dental prosthesis model. The preformed space can be defined by a three dimensional print of the refined digital dental prosthesis model. In another embodiment, the dental prosthesis is fabricated by rigidly attaching preformed prosthetic teeth to a predesigned abutment on the acrylic base of the dental prosthesis. The base of the dental prosthesis is fabricated by precision milling of preformed blocks of high density and high strength acrylic material. Each of the preformed prosthetic teeth that is attached to the base of the dental prosthesis has a shape of a dental crown.

In an embodiment, the base and framework of an existing or prefabricated dental prosthesis are modified for maximizing retention and function of the prefabricated dental prosthesis by adapting the base to the soft oral tissues of the patient and providing anchorage with intra-oral dentition, for example, adjacent teeth or implants.

The method and system disclosed herein combines three dimensional (3D) X-ray imaging, high resolution digital scanning, and three dimensional image data analysis to offer a highly accurate model-less technique to design and fabricate a dental prosthesis with predictable long term results. The advantages of the 3D digital model-less method of fabricating dental restorations include precision, consistency of quality and significantly less time for clinical intervention. The precision of digital technology in the anatomy, margins, contours, contacts, and occlusion makes it possible to design new retention features, and offer new and superior fabrication methods and materials compared to the traditional clinical methods. The method and system disclosed herein may be standardized to reduce the clinical time and cost of the treatments. The design and fabrication of the dental prosthesis according to the method and system disclosed herein provide ultimate precision, function, consistency, comfort and strength, maximize retention, enable customization of esthetics, allow exact jaw relations, and can be achieved in a single patient visit. The accuracy of digital analysis and design according to the method and system disclosed herein enables dentists to fabricate removable esthetic prostheses that can provide better retention, shade and teeth alignment to the patient. Also, the digital 3D data can be prescribed by dentists and forwarded to remote dental labs to analyze, calculate, design, and fabricate the dental prosthesis.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
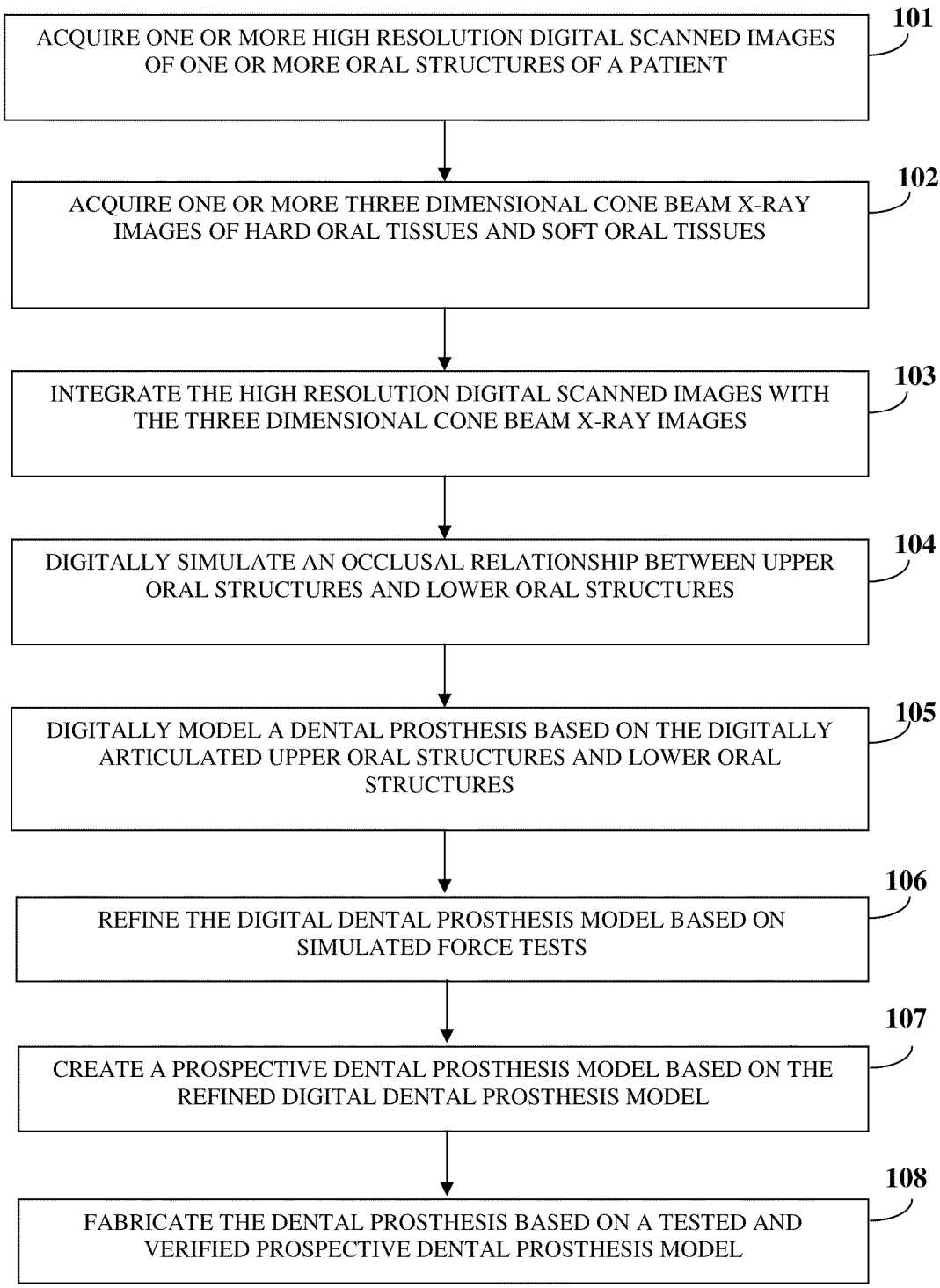
FIG. 1 illustrates a method for fabricating a dental prosthesis for a patient.
Figure 2A:
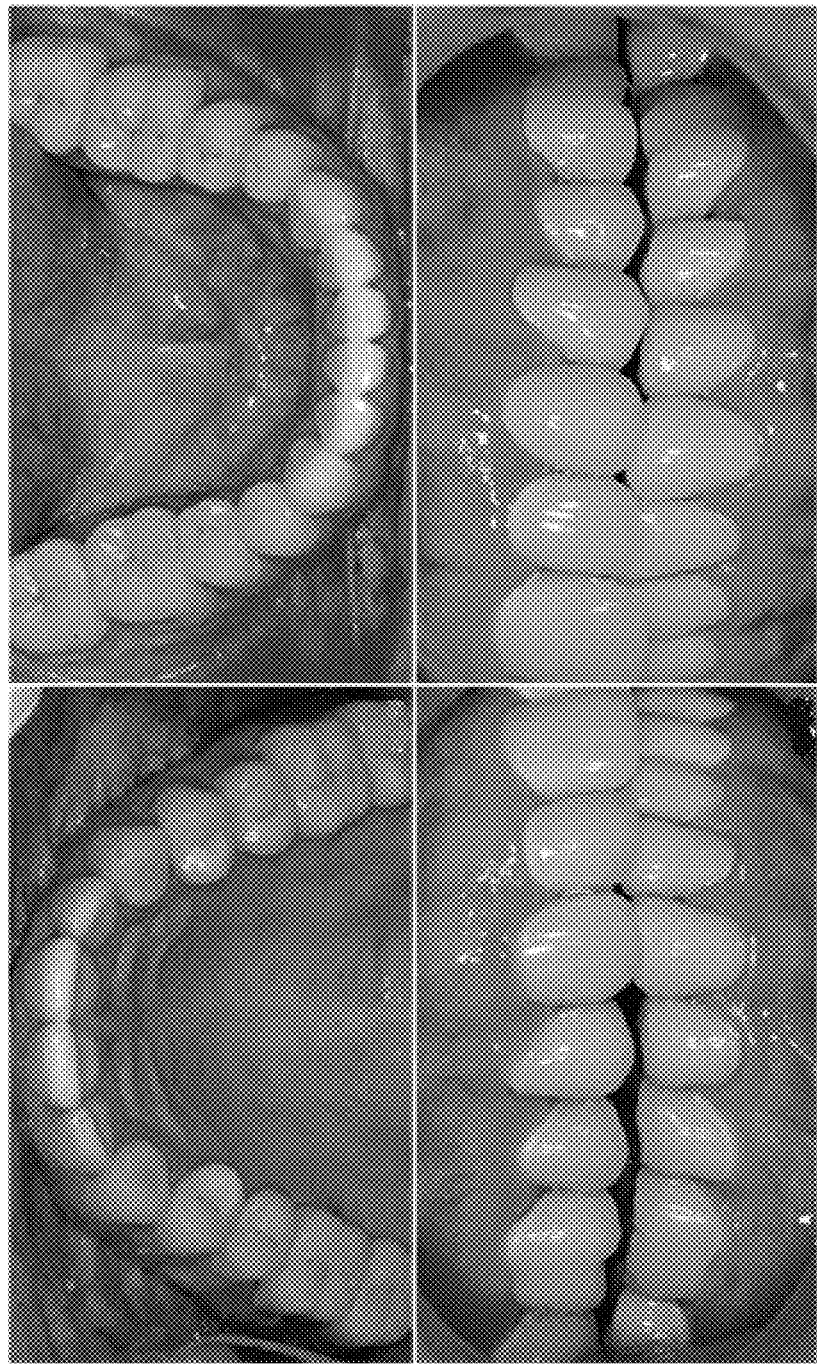
FIG. 2A exemplarily illustrates high resolution intra-oral scanned images of oral structures of a patient.
Figure 2B:
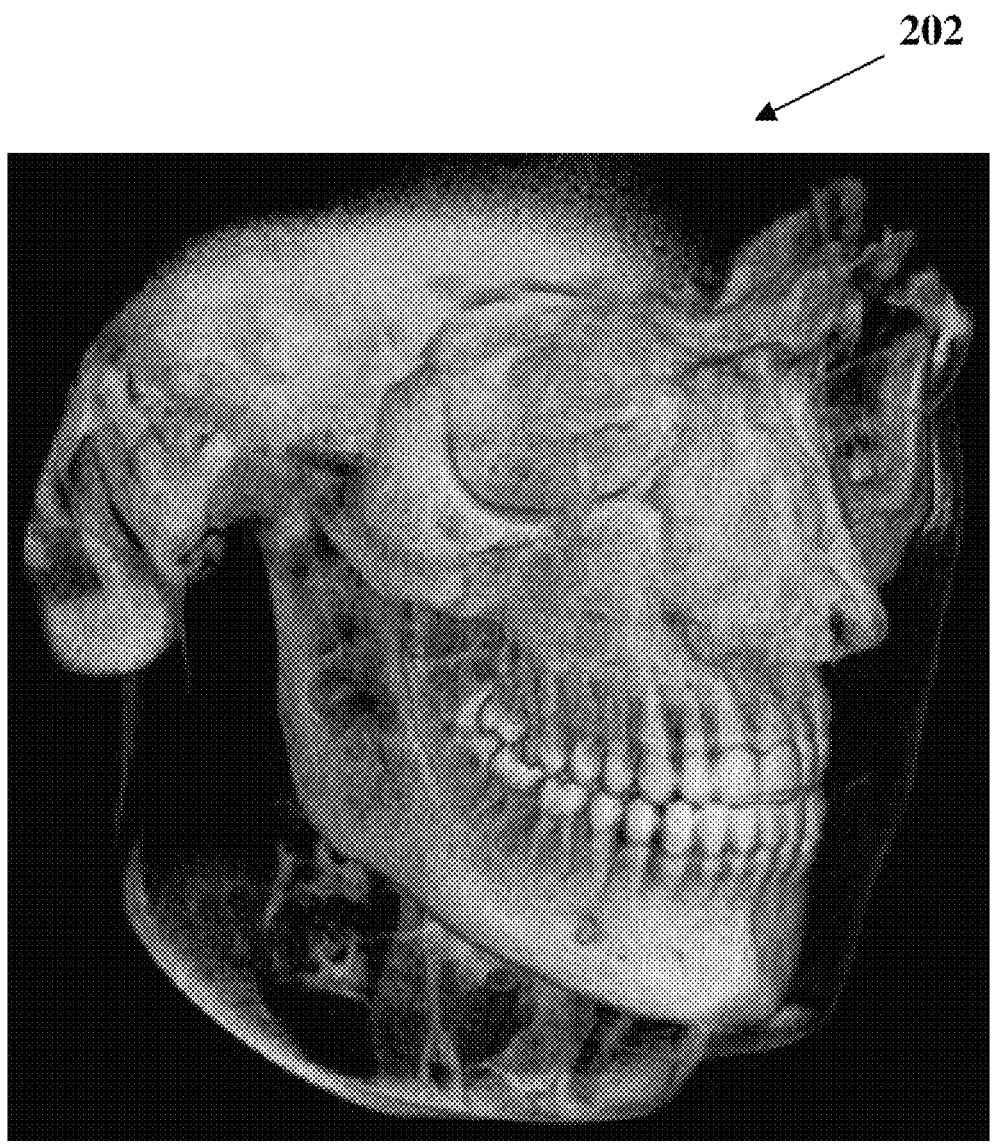
FIG. 2B exemplary illustrates a three dimensional cone beam X-ray image of hard oral tissues and soft oral tissues of a patient.
Figure 2C:
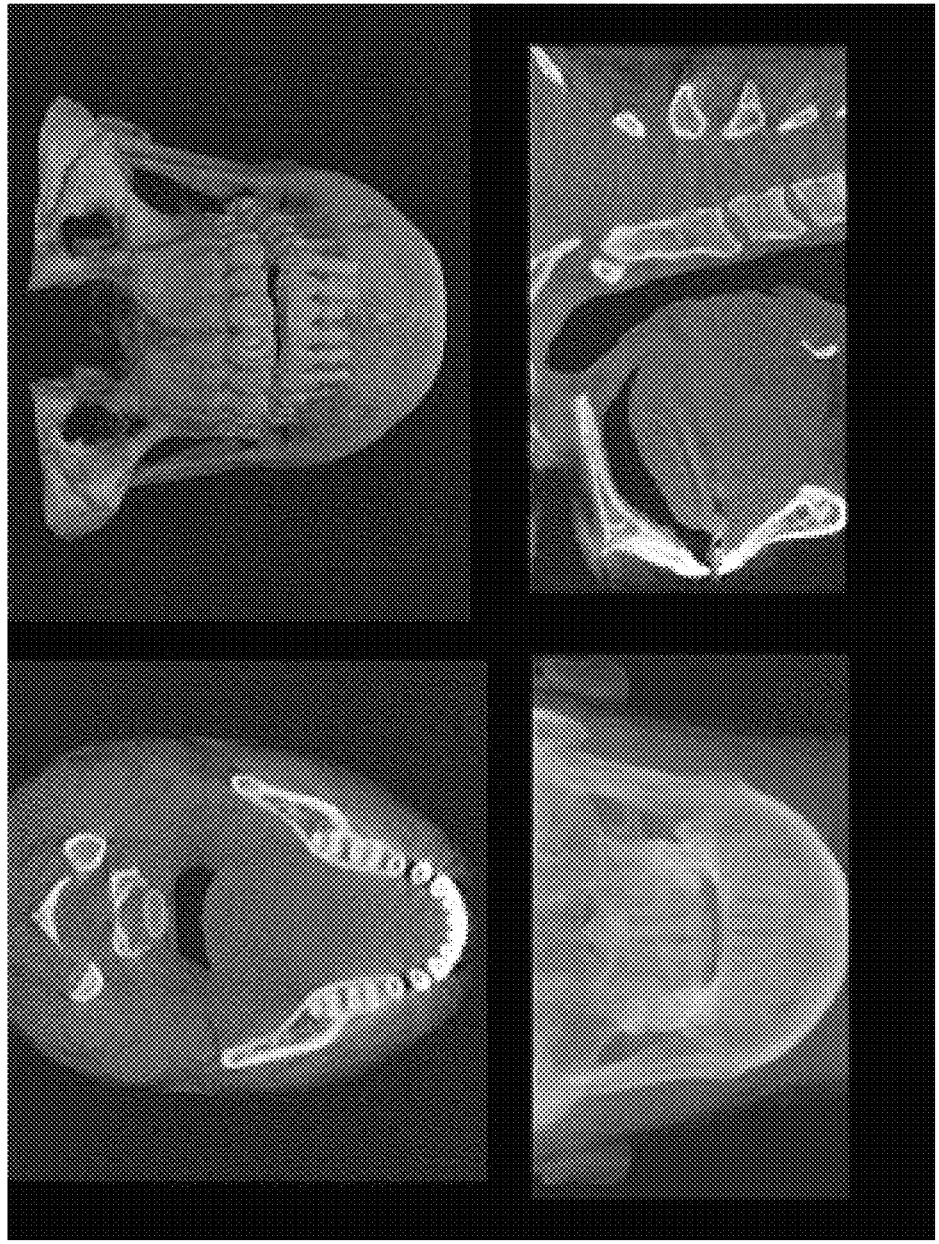
FIG. 2C exemplarily illustrates combined three dimensional images of oral structures of a patient.

FIG. 1 illustrates a method for fabricating a dental prosthesis for a patient. One or more three dimensional high resolution digital scanned images 201 of one or more oral structures of the patient, as exemplarily illustrated in FIG. 2A, are acquired 101 using one or more digital image scanning devices. The oral structures are, for example, the maxillary and mandibular bone and dentition of the patient. One or more three dimensional cone beam X-ray images 202 of hard oral tissues and soft oral tissues of the patient, as exemplarily illustrated in FIG. 2B, are acquired 102 using a cone beam X-ray image device. The high resolution digital scanned images 201 of the oral structures are integrated 103 with the three dimensional cone beam X-ray images 202 of the hard oral tissues and the soft oral tissues of the patient in a three dimensional space to obtain one or more combined three dimensional images of the oral structures of the patient. FIG. 2C exemplarily illustrates combined three dimensional images 203 of the oral structures of a patient. The combined three dimensional images 203 render low resolution images of upper jaw bones and lower jaw bones, roots of teeth, and temporomandibular joint complex, and high resolution images of coronal portion of the teeth and the soft oral tissues that potentially interface with the dental prosthesis. The occlusal relationship between upper oral structures and lower oral structures are digitally simulated 104 using the combined three dimensional images 203 for digitally articulating the upper oral structures and the lower oral structures. The occlusal relationship between the upper oral structures and the lower oral structures is digitally simulated at different functional condylar positions for digitally reproducing bite registration, centric occlusion, and centric relation. As used herein, a digital bite registration is a digital record or imprint of the opposing teeth of the patient's dentition when the upper jaw and lower jaw are in a closed position. The centric occlusion is the occlusion that results when the teeth of the patient are fit together in maximum intercuspation. The centric relation is the relationship of the upper jaw and the lower jaw when the head of the condyle is situated as far superior and anterior within the mandibular fossa.

The dental prosthesis is digitally modeled 105 based on the digitally articulated upper oral structures and lower oral structures to generate a digital dental prosthesis model for planning intra-oral positioning and structure of the dental prosthesis. The intra-oral positioning and the structure of the dental prosthesis are planned for achieving optimal occlusion, retention, smile profile, and for meeting phonetic requirements of the dental prosthesis. In an embodiment, a preliminary digital model of the dental prosthesis is established using pre-scanned digital models from an image database of dental prosthesis design. The preliminary digital model of the dental prosthesis is established by matching the pre-scanned digital models with jaw morphology and configuration of the patient obtained by characterizing arch form and size of upper and lower jaws, ridge height and form, and inter-jaw space and relation. The preliminary digital model of the dental prosthesis is also established by simulating and parameterizing elastic response of the soft oral tissues, occlusion force interaction between the upper teeth and the lower teeth, condylar guidance, lifting force of the upper lip and the lower lip, tongue motion, and oral muscles during primary motions of the oral structures of the patient.

The digital dental prosthesis model is refined 106 based on simulated force tests performed for assessing interference between different components of the digital dental prosthesis model with each other and with the oral structures of the patient, and retention of the digital dental prosthesis model. The simulated force tests are performed for reducing the interference and enhancing retention of the digital dental prosthesis model by simulating predetermined motions of the oral structures. The digital dental prosthesis model is refined by modifying position, alignment and height of teeth of the digital dental prosthesis model.

A prospective dental prosthesis model is created 107 based on the refined digital dental prosthesis model. The prospective dental prosthesis model is a physical three dimensional model for the dental prosthesis. The prospective dental prosthesis model is tested for verifying predetermined functions, for example, retention of the prospective dental prosthesis model, esthetics of the prospective dental prosthesis model, and occlusion and phonetics of the prospective dental prosthesis model. Testing the prospective dental prosthesis model comprises analyzing and incorporating modifications into the refined digital dental prosthesis model, creating a modified prospective dental prosthesis model, and verifying the modified prospective dental prosthesis model. The dental prosthesis is fabricated 108 based on the tested and verified prospective dental prosthesis model. In an embodiment, the dental prosthesis is fabricated by rigidly attaching preformed prosthetic teeth to a predesigned abutment on an acrylic base of the dental prosthesis. Each of the preformed prosthetic teeth has a shape of a dental crown. The base of the dental prosthesis is fabricated by precision milling of preformed blocks of high density and high strength acrylic material. The fabricated dental prosthesis is, for example, a removable complete denture dental prosthesis, a removable partial denture dental prosthesis, and a detachable fixed dental prosthesis anchored on natural oral structures or implanted oral structures.

Figure 3:
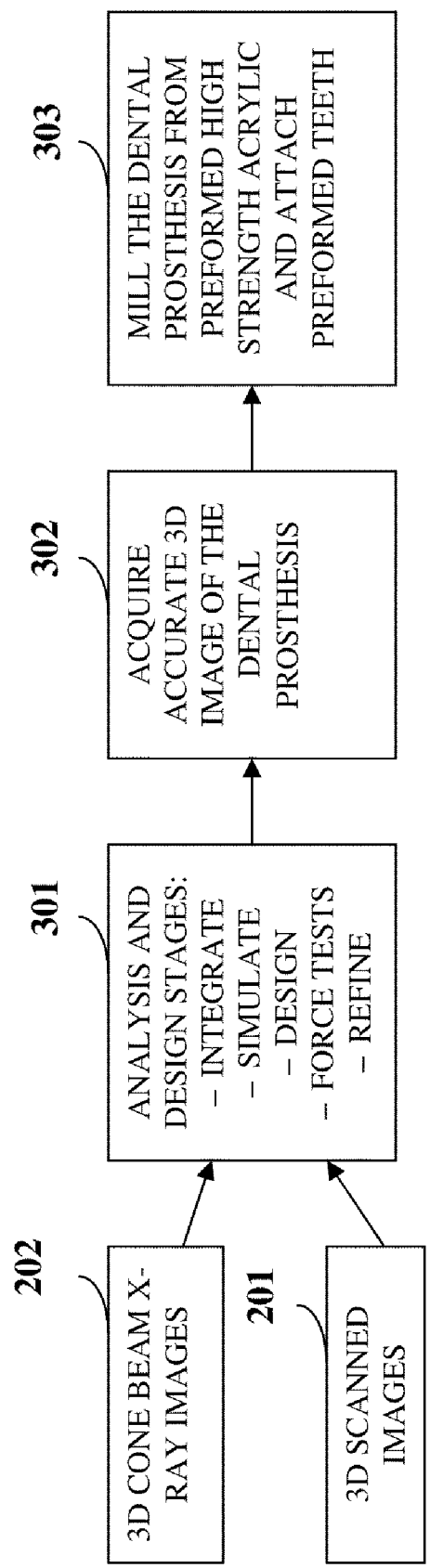
FIG. 3 exemplarily illustrates a block flow diagram for fabricating a dental prosthesis.

FIG. 3 exemplarily illustrates a block flow diagram for fabricating a dental prosthesis. The data acquisition, data analysis, and design of the dental prosthesis are performed in stages 301, for example, image integration, simulation, design, force tests, and design refinement. The data acquired comprises, for example, the three dimensional (3D) cone beam X-ray images 202 and the three dimensional (3D) scanned images 201. The acquired data is digitally integrated for analysis and design of the dental prosthesis. An accurate 3D image of the dental prosthesis is acquired 302 through stages of image creation, analysis, and processing. Preformed high strength acrylic material that constitutes the dental prosthesis is subjected to milling 303 using the acquired 3D images before attaching the preformed teeth.

Three dimensional (3D) cone beam X-ray images 202 provide three dimensional images of hard oral tissues and soft oral tissues comprising the maxillary and mandibular bone and dentition, the temporomandibular joint (TMJ), and soft tissues including the upper lip and lower lip. The 3D image data contains accurate three dimensional data of the upper jaw in relation to the maxilla, the lower jaw, and the condyle. The method and system disclosed herein analyzes the 3D image data to digitally accomplish a face bow transfer in a three dimensional virtual space with high accuracy.

The three dimensional (3D) image data of the lower jaw is separated from the 3D image data of the upper jaw, and then digitally integrated or brought together through accurate occlusion relations such as centric relation through proper condylar movement. The movement of the lower jaw is digitally simulated and animated through the occlusal relationships. The three dimensional jaw relations incorporates the exact dimensions of the jaw, is completely adjustable, and free from interference from masticular muscle groups. The digital occlusal relationships are used to set up teeth along the ridge, without impressions, model casts, manual face bow transfer, or bite registration. For edentulous patients or patients with temporomandibular joint (TMJ) disorders, the method disclosed herein accurately establishes the occlusion to create dentures or cure or treat TMJ disorders.

The resolution (approximately 100 µm) in the three dimensional (3D) cone beam X-ray images 202 is sufficient to establish the jaw relation, and the positions of the soft tissues such as the upper lip line. Although, these images 202 can be used to establish the esthetic requirements, they are not adequate to establish a tight seal and fit to the soft tissue and teeth surface. The method disclosed herein enables high resolution three dimensional digital scanning (approximately 20 µm-30 µm) to acquire the accurate three-dimensional data of the tissue and teeth that potentially interface with the dental prosthesis. Unlike the traditional impressions with alginate or silicone and plaster models that require multiple clinical appointments, the 3D scanning disclosed herein instantly provides accurate and undistorted digital images 201 of the oral tissues and teeth. In order to capture high resolution digital scanned images 201 of the oral tissues, for example, the maxillary area, patients are instructed to open their mouths wide with lips pulled forward, while saying "Ah". Similarly, for the mandibular area, patients are instructed to open wide with their lip pulled forward with the tongue touching the roof of their mouth. In the absence of the patient, the high resolution digital scan is performed using a teeth model or impression of the patient. In an embodiment, pictures of the smile profile of the patient, the color of the face, lip, gum tissue, and the shade of teeth are acquired for reference.

The method and system disclosed herein utilizes the three dimensional scanned image data to modify the design of a base and anchor of the dental prosthesis to create and maintain a tight seal and fit to the oral tissues during oral movements or activities, for example, chewing, biting, laughing, and different tongue movements.

Furthermore, the method and system disclosed herein integrates the three dimensional digital scanned images 201 with the three dimensional cone beam X-ray images 202 to create accurate three dimensional data models that simulate oral movements or tasks, for example, laughing or biting large edible objects, etc. The cone beam X-ray images 202 are integrated with the high resolution digital scanned images 201 of the dentition and soft tissue in a three-dimensional space. Multiple common discrete three dimensional reference data points, for example, the incisal edge of the same front teeth, are identified in both the cone beam X-ray images 202 and the high resolution digital scanned images 201. These reference points are used to convert individual image data into the common three dimensional space. The combined three dimensional images 203 comprise low resolution images of the upper and lower jaw bone, the roots of the teeth, and the temporomandibular joint complex, and high resolution images of the coronal portion of the teeth and the soft tissue that potentially interface with the dental prosthesis.

Figure 4A:
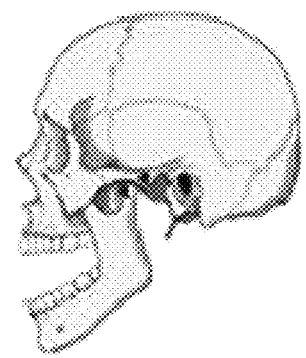
FIG. 4A exemplarily illustrates a three dimensional simulation of a lower jaw of a patient.
Figure 4B:
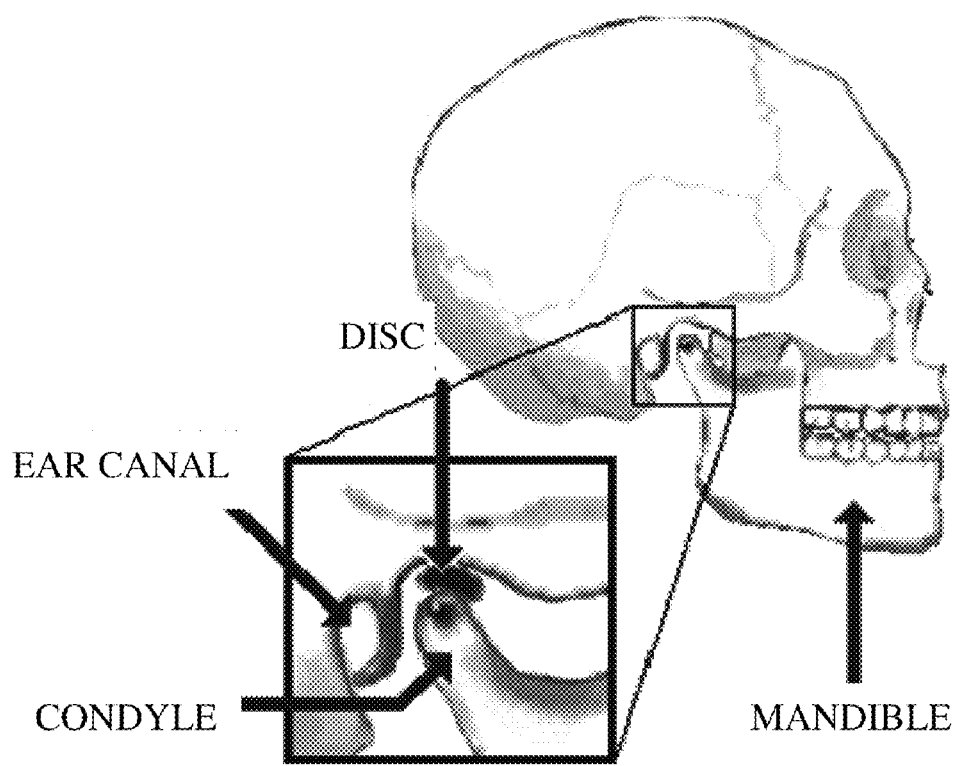
FIG. 4B exemplarily illustrates a three dimensional simulation of the movement of the condyle of a patient.

The three dimensional (3D) images of the lower jaw, including the lower teeth and the soft tissue are assembled together in a single group, and used to simulate the independent movement of the lower jaw as a rigid body. FIG. 4A exemplarily illustrates a three dimensional simulation of a lower jaw of a patient. When the lower jaw moves, the region that appears to morph is the soft tissue between the upper and lower jaws, specifically the two cheeks. As the jaw moves, the condyle translates digitally back and forth along the condylar process, and the lower jaw rotates digitally around the condyle. FIG. 4B exemplarily illustrates a three dimensional simulation of the movement of the condyle. The tips of the incisors follow a tear drop shape trajectory. This movement simulates the centric occlusion when the condyle is positioned in the most superior and posterior positions while the upper and lower jaws are close together. Hence, the facial bow, bite registration and centric relation are digitally reproduced with absolute accuracy. An ideal occlusion also requires occlusal contacts in all the teeth, with lighter contacts in the anterior region, heavier contacts in the posterior region, and smooth contacts during lateral excursion motion. Mechanical articulators estimate occlusion with fixed jaw portion and limited condylar motion and hence lack the accuracy and detail of the three dimensional digital simulation disclosed herein.

The three dimensional simulations are used to analyze the forces involved in the oral tasks for planning the optimal prosthesis designs that maximize the retention and stability of the dental prosthesis. The teeth of the dental prosthesis are set digitally in positions that stabilize the dental prosthesis, while maintaining perfect occlusion and esthetics. The base and metal frame are added to the design of the teeth, enabling sufficient support to the root of the teeth, while occupying minimal space and maintaining smooth contour and tight seal or fit to the anchoring tissue.

Figure 5:
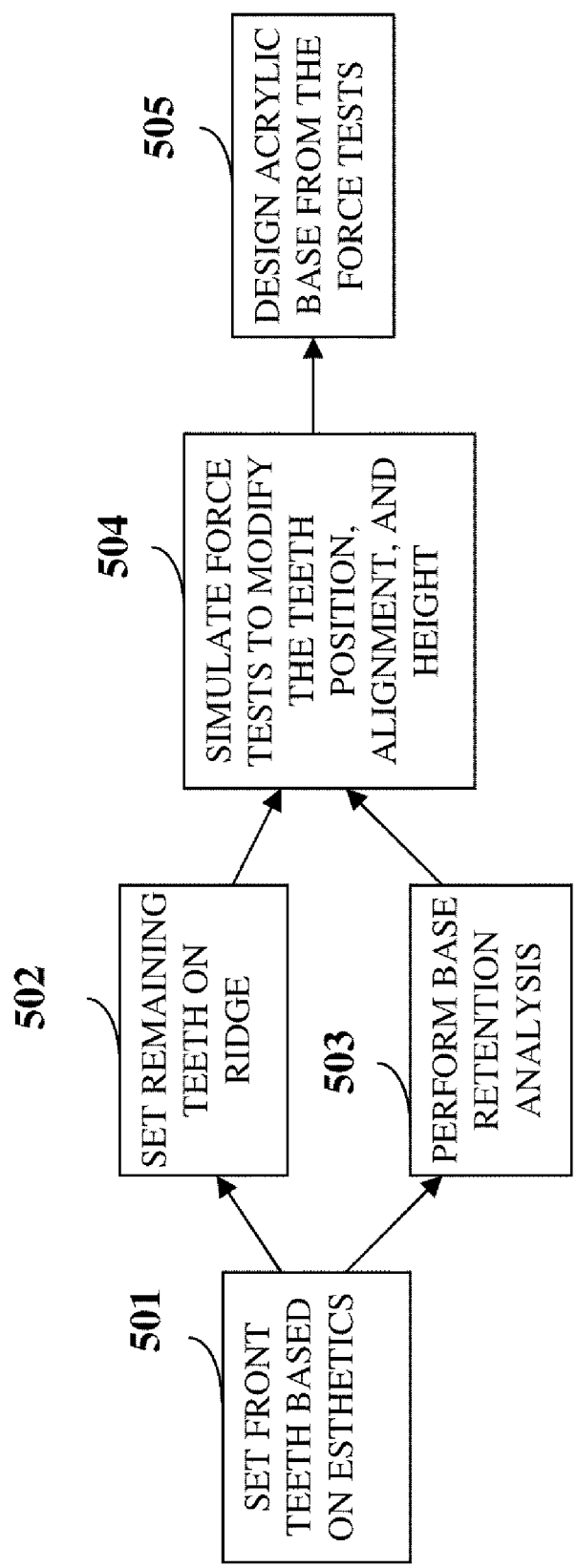
FIG. 5 exemplarily illustrates a block flow diagram summarizing a process for digitally designing the dental prosthesis.

FIG. 5 exemplarily illustrates a block flow diagram summarizing a process for digitally designing the dental prosthesis. The optimal perception of smile is characterized largely by the relative position of the edges of upper teeth and lower teeth to the upper lip and lower lip, and the shape and shade of the teeth. In designing the smile profile, factors that are considered comprise, for example, the shape of the teeth, width of the teeth, mid-line of the teeth, amount of teeth showing at resting position and smiling position, etc. The shape of the teeth is usually the inverse shape of the patient's face. At the resting position, the teeth edges are more pronounced to provide or retain a young appearance of the subject patient. The front teeth are digitally set 501 primarily based on esthetics. Different sizes, shapes, and shades of custom-made denture teeth are digitally scanned and stored in an image database.

In an embodiment, an image database comprising multiple forms of predetermined configuration of teeth and denture design is parameterized by the characteristics of the patients' dentitions and upper jaw and lower jaw of the patients. Once the combined three dimensional (3D) image data of patient is acquired, the characteristics of the dentition and the upper and lower jaw can be matched with the image database, and the preliminary design of the dental prosthesis can be generated instantly from the image database.

The pre-scanned teeth are digitally aligned or set 502 along the ridges for digitally modeling the dentures or partial dentures by following the basic principles of removable prostheses, for example, curve of Spee and curve of Wilson for the posterior teeth. The first choice of teeth position is the original position of the missing teeth. Since there are minimal restrictions on the positioning of the teeth, several factors, for example, optimal customized esthetics can alter the teeth position based on the prescription of the restoring dentists. For example, the midline between the central incisors has to match the upper facial midline of the nose, and the width of the nose has to match with the distance between the two canines. The digital modeling and simulation of the method disclosed herein enables the dentist to recreate a customized smile for the patient.

The teeth are digitally set to match the oral conditions of the patients by characterizing the arch form and size of the upper jaw and lower jaw, the ridge height and form, the inter-jaw space and relation, and the other oral and facial structures. Based on the digitally placed teeth position, the interfering forces and the retention forces are analyzed and quantified using basic laws of physics. The numerical data acquired is further analyzed to generate the correct shape of the dental prosthesis that will enhance the retention, esthetics, function, and phonetics of the dental prosthesis.

The base of the dental prosthesis is designed for complete peripheral air tight seal with the hard oral tissues and the soft oral tissues to achieve suction based retention of the dental prosthesis. Traditionally, many patients depend on denture adhesives to maintain an air seal which may cause infection on the teeth and gum. The negative air pressure generated by the suction force of the air pocket created from the air tight seal between the oral tissues and the dental prosthesis is the main source of retention, especially for complete dentures. The air pocket is around 1 mm-2 mm deep. The suction force of the air pocket is dependent on the area of the air pocket. The forces and movements of the oral activities can cause the dental prosthesis to move away from the original position. The base of the dental prosthesis is designed to maintain the air pocket seal during these normal functional movements. The seal is tighter towards the edge of the dental prosthesis. The center portion of the sealed area is slightly recessed to form the air pocket for the suction. The design of the base provides a retentive seal on the lower jaw, as long as an air tight seal is retained. The air pocket is designed to resist the forces during normal functional movements. However, the patient can remove the denture by applying a sideways force that seldom occurs during normal function. The force to remove the dental prosthesis is directly applied from the side to release the air pocket and remove the dental prosthesis.

Figure 6:
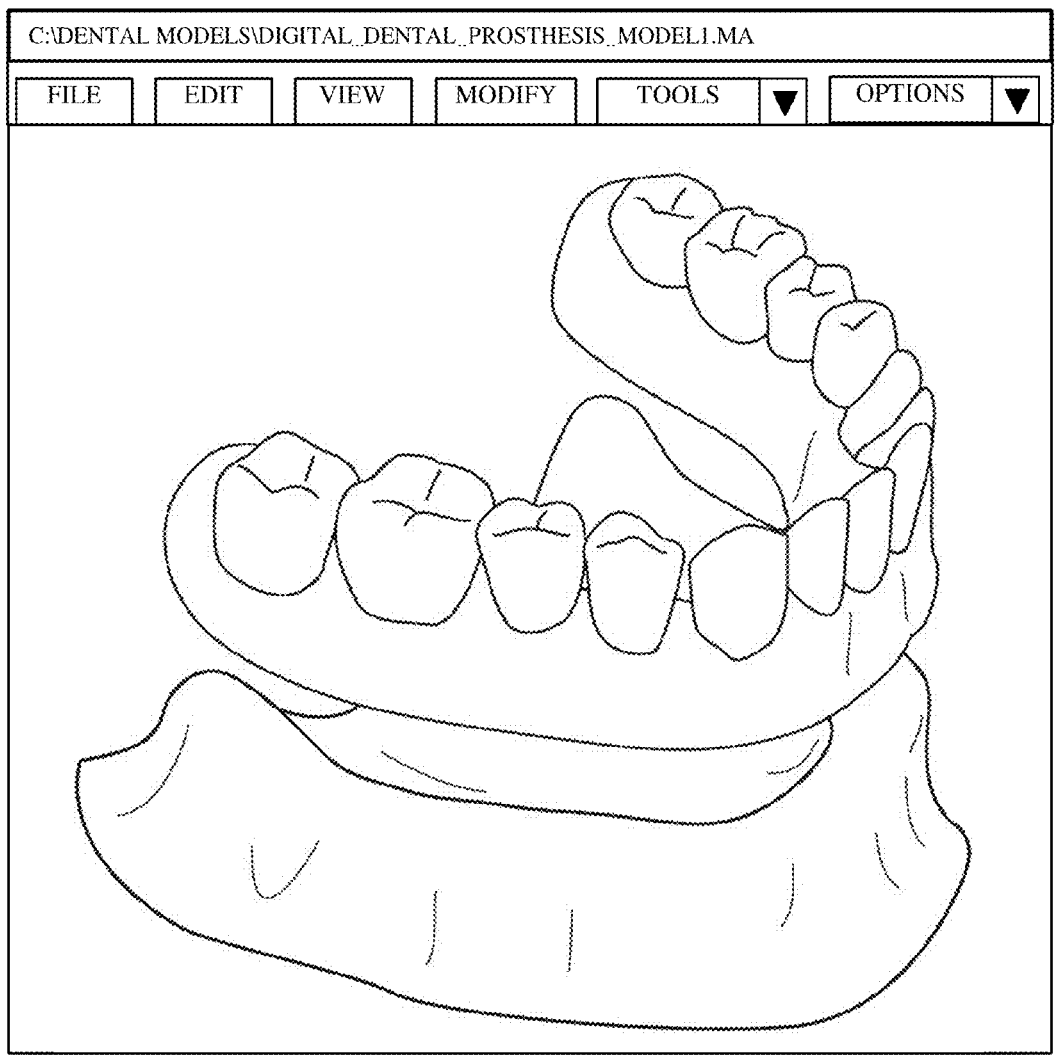
FIG. 6 exemplarily illustrates a digitally modeled dental prosthesis.

The image database containing pre-scanned and pre-stored digital models that match different jaw morphology and configuration is referenced to the patient to establish one or more pre-stored models as a preliminary digital model for the patient to begin with. In determining the digital dental prosthesis model, the elastic response of the soft tissue, the occlusion force interaction between the upper teeth and lower teeth, the condylar guidance, the lifting force of the upper lip and lower lip, the tongue motion, and other muscles during functional motions such as laughing, chewing and biting large objects are parameterized and simulated. FIG. 6 exemplarily illustrates a digitally modeled dental prosthesis. By leveraging the convenience and power of digital calculation and simulation, the method and system disclosed herein incorporates a testing interface comprising testing modules with buttons to simulate and conduct force tests for assessing and analyzing 503 retention of the designed dental prosthesis during important motions and functions such as laughing, chewing, biting large edible objects, lip lifting, tongue pushing, etc. The digital dental prosthesis model is refined based on the simulated force tests 504 to modify position, alignment and height of teeth of the digital dental prosthesis model.

Figure 7:
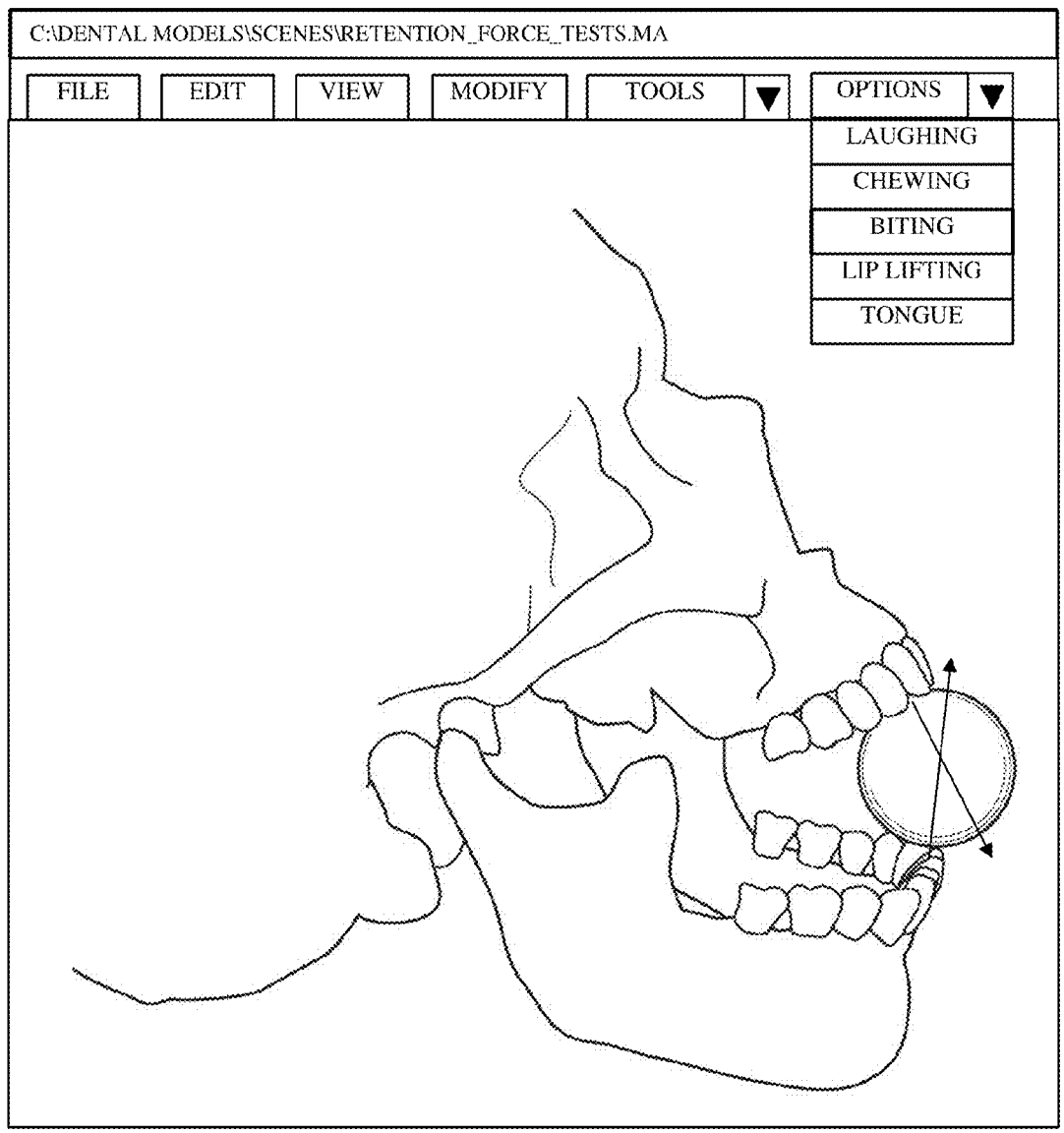
FIG. 7 exemplarily illustrates simulated force test modules for assessing a digitally modeled dental prosthesis.

Multiple software applications for three dimensional computer-aided design (CAD) and animation may be used for modeling, animating, simulating, and rendering the digital dental prosthesis model. One such software application is Autodesk Maya® of Autodesk® Inc, although any CAD and animation software can be used. FIG. 7 exemplarily illustrates simulated force test modules for assessing a digitally modeled dental prosthesis. The force test modules for simulating and rendering the functions such as laughing, chewing, biting, lip lifting, and tongue movements are configured using the software application. FIG. 7 specifically illustrates an example of the digital dental prosthesis model rendering a biting scene. The design of the digital dental prosthesis model is refined based on the simulated force tests. Optimal configurations of the teeth are established to maximize the retention of the dental prosthesis. For example, shorter teeth height reduces the interference forces that cause the dental prosthesis to dislocate from the jaw. For partial dentures, shorter contact area of the dental prosthesis to the gum results in stronger anchorage force. In the traditional partial denture designs, the retention features can be added only to those areas that are visible and accessible. In the method and system disclosed herein, retention features can also be added to areas under the partial dentures that are not visible and accessible.

After the teeth positions are determined, the acrylic base of the dental prosthesis is incorporated into the design 505 to provide a solid support to the teeth, smooth flow of contour, and minimal space occupation. The acrylic base may be designed or digitally modeled based on the simulated force tests as disclosed in the detailed description of FIG. 7. Generally, the acrylic layer forms a thin layer over the oral tissue. However, occasionally the acrylic material is used to fill space in the sagging cheek area to improve facial appearance.

In an embodiment, the digital design of the dental prosthesis is based on preformed crowns that are attached to predesigned abutments from the acrylic base, similar to the crown restorations for natural teeth. The acrylic base or the metal frame of the dental prosthesis is created in a bulky form that is easy to cast or mold. The detailed adjustments and modifications for the dentures or the metal frame for partial dentures are made through a precision milling process disclosed in the detailed description of FIG. 8.

The three dimensional digital model of the dental prosthesis is printed using a three dimensional (3D) printer using a biologically safe material to create a prospective dental prosthesis model. The digital model comprises, for example, pre-scanned teeth attached to the abutments on the dental prosthesis. The provisional or prospective dental prosthesis model is tested similar to a try-in appointment by the patient to verify predetermined functions, for example, the esthetics, the centric relation and occlusion, and the phonetics. Phonetics is an important factor in the design of the teeth position. At the resting position, the upper teeth should be slightly in contact with the lower lip to provide a proper seal for "f" and "s" sounds. Vertical space and tongue space should be considered according to the size of the tongue for proper phonetics. Moreover, the patient should not have any trouble swallowing. The patient may be instructed to count numbers from 1-40, 60-70, and special attention is given to the "f" and "s" sounds. The design of the digital dental prosthesis model is refined based on the trial inputs and suggestions. The digital dental prosthesis model is refined by analyzing and incorporating the required modifications, and further verified.

High resolution three dimensional print of the dental prosthesis can be generated from the three dimensional image model of the dental prosthesis. The traditional methods of investing a preformed space using the three dimensional print and casting, or polymerizing under high pressure or injecting materials into the space for fabricating the dental prosthesis are within the scope of the method disclosed herein. The preliminary fabricated prosthesis is further milled and polished in a precision guided milling chamber as exemplarily illustrated in FIG. 8.

In an embodiment, a preformed block of high density and high strength acrylic material or other biologically compatible material are used for the dental prosthesis. The preformed material is stronger and is used to create thinner, stronger and esthetic removable dental prosthesis. The prosthetic teeth are preformed in the shape of a dental crown and attached to the abutment predesigned on the base of the dental prosthesis. This method substantially eliminates the delays due to the dental lab processes and save time in fabricating the dental prosthesis. Accordingly, the design and fabrication of the dental prosthesis can be finished in a single patient visit.

The design of the metal framework for partial dentures is prescribed by the restoring dentists. The metal framework can be cast using the traditional casting method, which allows the melted metal to flow into a preformed space. Also, the acrylic material can be molded by injecting and pouring the acrylic material into a preformed space of the three dimensional print of the refined digital dental prosthesis model for fabricating the dental prosthesis.

Figure 8:
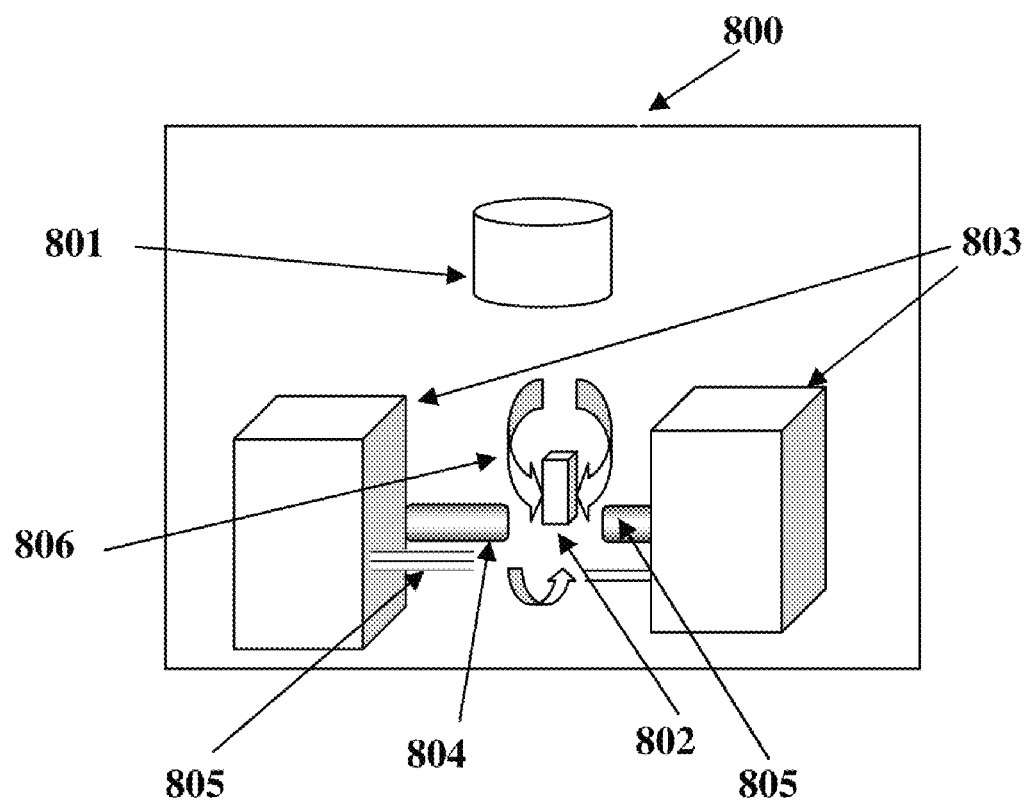
FIG. 8 exemplarily illustrates a milling chamber for milling the dental prosthesis.
Figure 9:
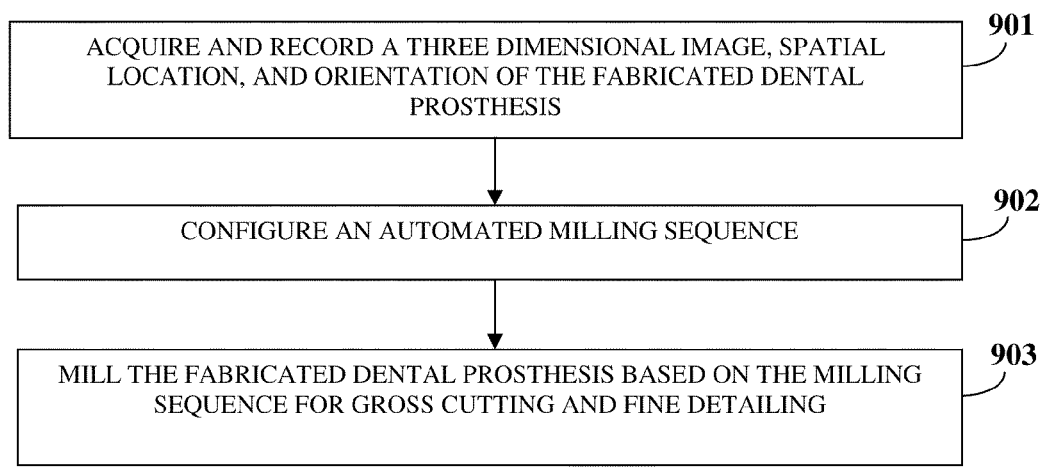
FIG. 9 exemplarily illustrates a method of subjecting the fabricated dental prosthesis to a milling process for gross cutting and fine detailing.

FIG. 8 exemplarily illustrates a milling chamber 800 for milling the dental prosthesis. The milling process is precision guided by the three dimensional image of the milling object in the milling chamber 800. Before milling, the pre-milled dental prosthesis 802 is required to be firmly mounted for processing. Three holding arms 806 are programmed based on the three dimensional images to clamp the fabricated dental prosthesis 802 on the front and the back sides without causing any distortion to the fabricated dental prosthesis 802 by the holding force. FIG. 9 exemplarily illustrates a method of subjecting the fabricated dental prosthesis 802 to a milling process for gross cutting and fine detailing. A separate three dimensional scan is performed to acquire and record 901 a three dimensional image, the spatial location, orientation and shape of the pre-milled fabricated dental prosthesis 802 using a digital image scanning device 801. The scanned image of the pre-milled fabricated dental prosthesis 802 is compared with the designed and refined digital dental prosthesis model, and an automated milling sequence is generated and programmed or configured 902 based on the exact spatial location of the pre-milled fabricated dental prosthesis 802. The fabricated dental prosthesis 802 is milled 903 into the exact shape of the refined digital dental prosthesis model.

The final details of the dental prosthesis 802 are created in the milling process. Two milling motors 803, each with gross milling and fine milling burs 804 and 805 are engineered to following the milling sequence, with water spray to cool down the heated material. After the milling is completed, the milled dental prosthesis is manually examined and polished with a polish agent, for example, pumice for ensuring a polished and smooth prosthesis base is produced to reduce irritation and increase retention through the air seal. In an embodiment, the acrylic material of the dental prosthesis is milled using a laser. Laser milling is precise, clean and easy to manage. However, laser milling is suited for flexible and soft material but not the solid dense material.

The method and system disclosed herein also enables repairing of old poorly fit prefabricated dentures and partial dentures. In this case, the digital images of the prefabricated prosthesis, the oral cavity of the patient, and three dimensional cone beam X-ray images 202 are acquired. A digital analysis and redesign of the prefabricated prosthesis enables dentists to improve the retention, esthetics, and function of the prefabricated prosthesis using the method disclosed herein. The milling process is used to reshape the prefabricated prosthesis to an ideal condition according to the digitally generated improved dental prosthesis with better retention, function and esthetics. The base of the existing prosthesis is modified to enhance the retention and function by precise adaptation to the soft tissue through an air tight seal. The metal frame work of existing partial dentures is modified to attain precise anchorage with existing natural dentition to provide passive and strong retention.

In an embodiment, a detachable implant-supported removable prosthesis is designed and fabricated for patients with implants, with precise attachment and ideal tissue seal. For patients with temporomandibular joint (TMJ) pain and discomfort, the accurate digital information of the condylar position during lower jaw movement is used to fabricate functional bite appliances to correct jaw relation and relieve the TMJ symptoms. In many cases, the TMJ related disorders are caused by dislocated discs or condyle due to the way the teeth occlude with each other. Using three dimensional (3D) X-ray imaging, the dislocation of the disc or condyle is determined and a new position for the lower jaw is digitally generated to move the discs or the condyle back to their proper position, and then design appliances that will place the lower jaw to the proper position. This may take multiple small steps to move the discs or condyle from a disordered position to the proper position. A series of functional bite appliances can be fabricated in a sequence to correct the dislocated disc over a period of time, until the disc returns to the proper location.

In an embodiment, by using accurate three dimensional (3D) images 201 and 202 with correct jaw relations, provisional esthetic appliances that enhance the esthetic appearance of the teeth, and orthodontic aligners that correct misaligned teeth can also be digitally modeled and fabricated according to the multiple digitally aided methods disclosed herein. For patients with discolored or malformed teeth who desire an instant makeover for the appearance of their teeth, a precise custom-made orthodontic esthetic appliance, for example, a hard tray that covers all the teeth from the facial side with white and straight appearance can be modeled from the high resolution 3D scan of the patient's teeth. These modeled esthetic appliances are more precise than lab fabricated appliances and are free of errors. For orthodontic aligners, the 3D cone beam X-ray images 202 of the jaws and the high resolution digital scanned images 201 of the teeth are used to propose a sequence of teeth movement, digitally generate the new positions of the teeth, and fabricate functional orthodontic appliances, for example, C-Guard appliances to reposition the teeth to their proposed positions.

Figure 10:
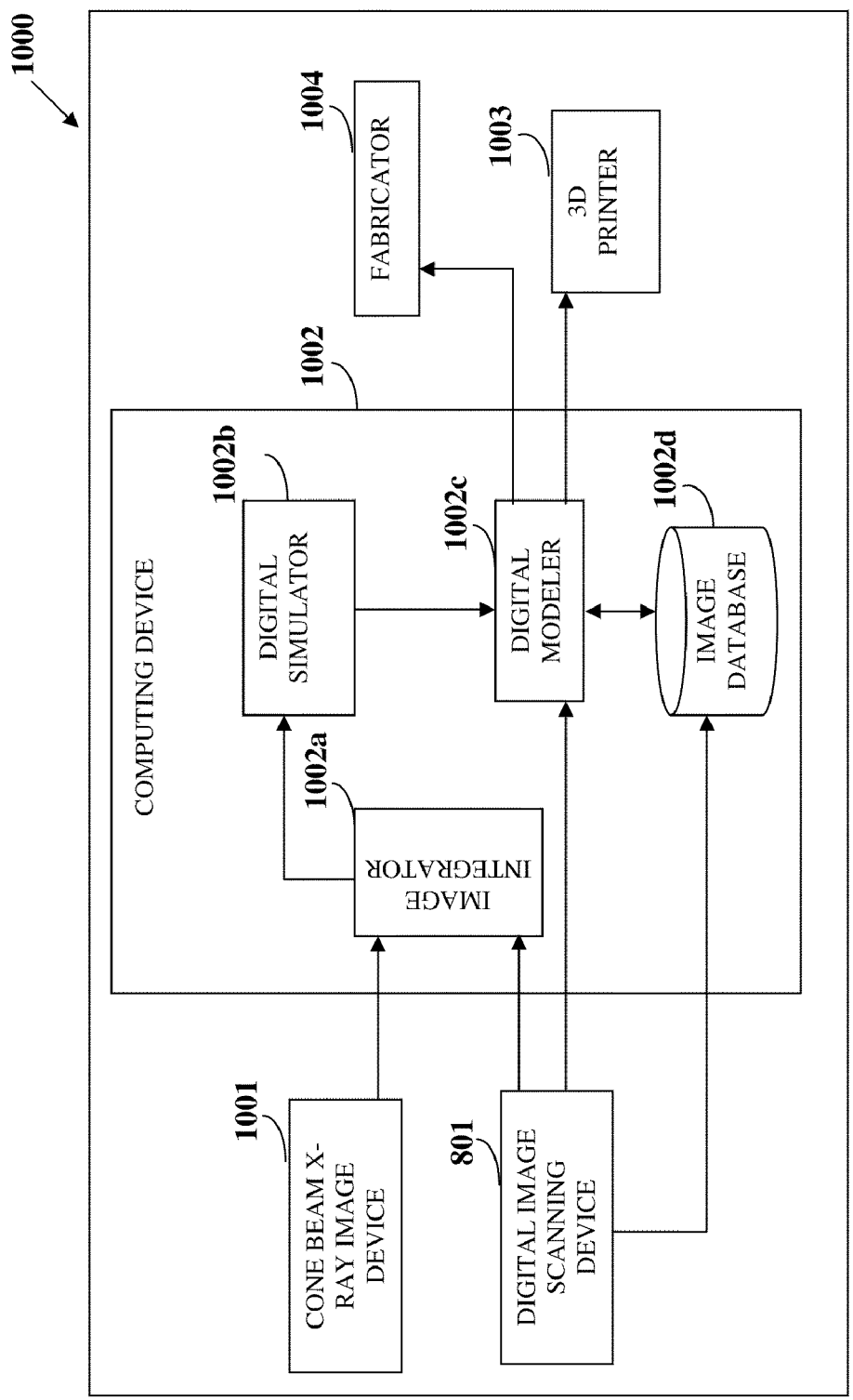
FIG. 10 illustrates a system for designing and fabricating a dental prosthesis for a patient.

FIG. 10 illustrates a system 1000 for designing and fabricating a dental prosthesis for a patient. The system 1000 disclosed herein comprises a digital image scanning device 801, a cone beam X-ray image device 1001, a three dimensional (3D) printer 1003, and a fabricator 1004. The system 1000 disclosed herein further comprises an image integrator 1002a, a digital simulator 1002b, and a digital modeler 1002c, and an image database 1002d provided on the computing device 1002. The digital image scanning device 801 acquires one or more high resolution digital scanned images 201 of one or more oral structures of the patient. The cone beam X-ray image device 1001 acquires one or more three dimensional cone beam X-ray images 202 of hard oral tissues and soft oral tissues of the patient. The image integrator 1002a provided on the computing device 1002 integrates the high resolution digital scanned images 201 of the oral structures with the three dimensional cone beam X-ray images 202 of the hard oral tissues and the soft oral tissues of the patient in a three dimensional space to obtain combined three dimensional images 203 of the oral structures.

The digital simulator 1002b provided on the computing device 1002 digitally simulates an occlusal relationship between upper oral structures and lower oral structures using the combined three dimensional images 203 for digitally articulating the upper oral structures and lower oral structures. The digital simulator 1002b digitally simulates the occlusal relationship between the upper oral structures and the lower oral structures at different functional condylar positions for digitally reproducing bite registration, centric occlusion, and centric relation.

The digital modeler 1002c provided on the computing device 1002 digitally models the dental prosthesis based on the digitally articulated upper oral structures and lower oral structures to generate a digital dental prosthesis model for planning intra-oral positioning and structure of the dental prosthesis. The digital modeler 1002c establishes a preliminary digital model of the dental prosthesis using pre-scanned digital models stored in the image database 1002d.

The image database 1002d comprises pre-scanned and pre-stored digital models of different dental prostheses based on multiple forms of dentition and upper and lower jaw configuration. The digital modeler 1002c establishes a preliminary digital model of the dental prosthesis by matching the pre-stored digital models with jaw morphology and configuration of the patient by characterizing arch form and size of upper and lower jaws, ridge height and form, and inter-jaw space and relation. In an embodiment, the digital modeler 1002c establishes the preliminary digital model of the dental prosthesis by simulating and parameterizing, for example, elastic response of the soft oral tissues, occlusion force interaction between the upper teeth and the lower teeth, condylar guidance, lifting force of the upper lip and the lower lip, tongue motion, and oral muscles during primary motions of the oral structures of the patient. The digital modeler 1002c refines the digital dental prosthesis model based on simulated force tests performed for assessing interference and retention of the digital dental prosthesis model. The digital simulator 1002b performs the simulated force tests for reducing interference and enhancing retention of the digital dental prosthesis model by simulating predetermined motions of the oral structures.

The three dimensional printer 1003 creates a prospective dental prosthesis model based on the refined digital dental prosthesis model. The prospective dental prosthesis model is tested in the dental clinic in a try-in session with the patient for verifying predetermined functions, for example, retention, esthetics, occlusion, and phonetics of the prospective dental prosthesis model. The fabricator 1004 fabricates the dental prosthesis based on the tested and verified prospective dental prosthesis model. The system 1000 disclosed herein is used to fabricate a removable complete denture dental prosthesis, a removable partial denture dental prosthesis, or a detachable fixed dental prosthesis anchored on natural oral structures or implanted oral structures. In an embodiment, the fabricator 1004 fabricates precision-driven removable temporomandibular joint appliances, esthetic appliances, and orthodontic aligners. The milling sequence in the milling chamber 800 is digitally programmed and precision-guided by digital scanning of the milling object, for example, the removable esthetic or functional appliance, the fabricated dental prosthesis 802, etc. in the milling chamber 800.

The digital modeler 1002c also digitally models an acrylic base of the dental prosthesis based on the simulated force tests. The digital modeler 1002c configures the acrylic base for establishing a complete peripheral air tight seal with the hard oral tissues and the soft oral tissues to achieve suction based retention of the dental prosthesis.

The fabricator 1004 fabricates a partial denture dental prosthesis by first casting metal into a preformed space of the prospective dental prosthesis model, then molding acrylic material into a preformed space of the prospective dental prosthesis model. In another embodiment, the fabricator 1004 fabricates the dental prosthesis by rigidly attaching preformed prosthetic teeth to predesigned abutment on an acrylic base of the dental prosthesis. The preformed prosthetic teeth in the shape of a dental crown are attached to the predesigned abutment on the dental prosthesis via mechanical locks, permanent adhesives or cements. The fabricator 1004 fabricates the base of the dental prosthesis by precision milling of preformed blocks of high density and high strength acrylic material.

Figure 11:
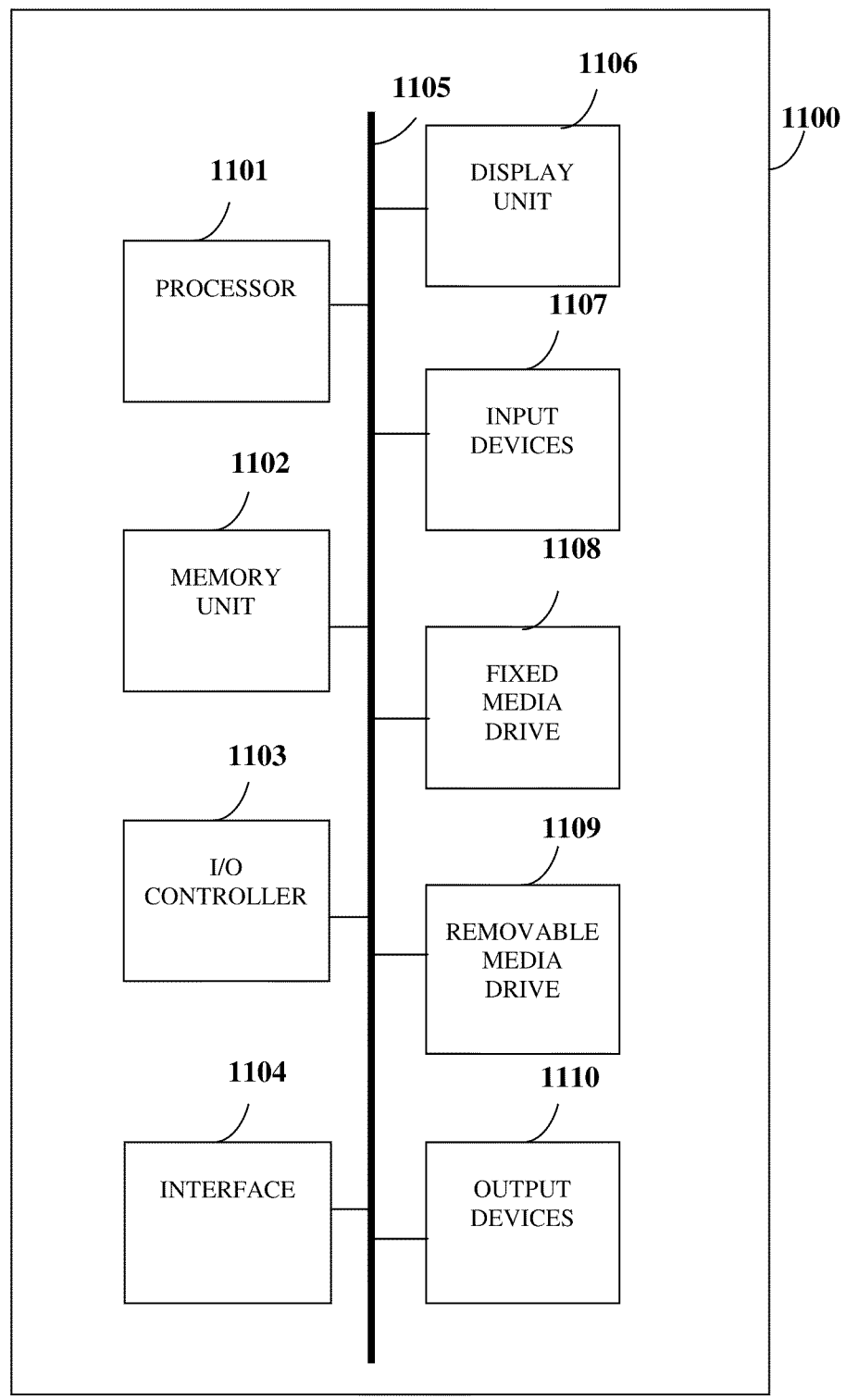
FIG. 11 exemplarily illustrates the architecture of a computer system used for modeling and fabricating a dental prosthesis for a patient.

FIG. 11 exemplarily illustrates the architecture of a computer system 1100 used for modeling and fabricating a dental prosthesis for a patient. The computer system 1100 comprises a processor 1101, a memory unit 1102 for storing programs and data, an input/output (I/O) controller 1103, and a display unit 1106 communicating via a data bus 1105. The memory unit 1102 comprises a random access memory (RAM) and a read only memory (ROM). The computer system 1100 further comprises one or more input devices 1107, for example, a keyboard such as an alphanumeric keyboard, a mouse, a joystick, etc. The input/output (I/O) controller 1103 controls the input and output actions performed by a user. The computer system 1100 communicates with other computer systems through an interface 1104, comprising, for example, a Bluetooth™ interface, an infrared (IR) interface, a WiFi interface, a universal serial bus interface (USB), a local area network (LAN) or wide area network (WAN) interface, etc.

The processor 1101 is an electronic circuit that can execute computer programs. The memory unit 1102 is used for storing programs, applications, and data. For example, the image integrator 1002a, the digital simulator 1002b, and the digital modeler 1002c are stored on the memory unit 1102 of the computer system 1100. The memory unit 1102 is, for example, a random access memory (RAM) or another type of dynamic storage device that stores information and instructions for execution by the processor 1101. The memory unit 1102 also stores temporary variables and other intermediate information used during execution of the instructions by the processor 1101. The computer system 1100 further comprises a read only memory (ROM) or another type of static storage device that stores static information and instructions for the processor 1101. The data bus 1105 permits communication between the modules, for example, 1002a, 1002b, and 1002c of the computer implemented system 1000 disclosed herein.

Computer applications and programs are used for operating the computer system 1100. The programs are loaded onto the fixed media drive 1108 and into the memory unit 1102 of the computer system 1100 via the removable media drive 1109. In an embodiment, the computer applications and programs may be loaded directly through the network. Computer applications and programs are executed by double clicking a related icon displayed on the display unit 1106 using one of the input devices 1107. The user interacts with the computer system 1100 using a graphical user interface (GUI) of the display unit 1106.

The computer system 1100 employs an operating system for performing multiple tasks. The operating system manages execution of, for example, the image integrator 1002a, the digital simulator 1002b, and the digital modeler 1002c provided on the computer system 1100. The operating system further manages security of the computer system 1100, peripheral devices connected to the computer system 1100, and network connections. The operating system employed on the computer system 1100 recognizes keyboard inputs of a user, output display, files and directories stored locally on the fixed media drive 1108, for example, a hard drive. Different programs, for example, a web browser, an electronic mail (email) application, etc., initiated by the user are executed by the operating system with the help of the processor 1101, for example, a central processing unit (CPU). The operating system monitors the use of the processor 1101.

The image integrator 1002a, the digital simulator 1002b, and the digital modeler 1002c are installed in the computer system 1100 and the instructions are stored in the memory unit 1102. The high resolution digital scanned images 201 and the three dimensional cone beam X-ray images 202 are transferred from the digital image scanning device 801 and the cone beam X-ray image device 1001 to the image integrator 1002a installed in the computer system 1100 of the computing device 1002 via the interface 1104 or a network. A user initiates the execution of the image integrator 1002a by double clicking the icon for the image integrator 1002a on the display unit 1106 or the execution of the image integrator 1002a is automatically initiated on installing the image integrator 1002a on the computer system 1100 of the computing device 1002. Instructions for modeling and fabricating a dental prosthesis for a patient are retrieved by the processor 1101 from the program memory in the form of signals. The locations of the instructions in the modules, for example, 1002a, 1002b, and 1002c, are determined by a program counter (PC). The program counter stores a number that identifies the current position in the program of the image integrator 1002a, the digital simulator 1002b, and the digital modeler 1002c.

The instructions fetched by the processor 1101 from the program memory after being processed are decoded. The instructions are placed in an instruction register (IR) in the processor 1101. After processing and decoding, the processor 1101 executes the instructions. For example, the image integrator 1002a defines instructions for integrating one or more digital scanned images 201 of the oral structures with one or more three dimensional cone beam X-ray images 202 of the hard oral tissues and soft oral tissues of the patient in a three dimensional space to obtain one or more combined three dimensional images 203 of the oral structures of the patient. The digital simulator 1002b defines instructions for digitally simulating occlusal relationships between upper oral structures and lower oral structures using the combined three dimensional images 203 for digitally articulating the upper oral structures and the lower oral structures. The digital modeler 1002c defines instructions for digitally modeling the dental prosthesis based on digitally articulated upper oral structures and lower oral structures to generate a digital dental prosthesis model. The digital modeler 1002c defines instructions for refining the digital dental prosthesis model based on simulated force tests performed for assessing interference and retention of the digital dental prosthesis model, etc. The instructions are stored in the program memory or received from a remote server.

The processor 1101 retrieves the instructions defined by the image integrator 1002a, the digital simulator 1002b, and the digital modeler 1002c, and executes the instructions.

At the time of execution, the instructions stored in the instruction register are examined to determine the operations to be performed. The specified operation is then performed by the processor 1101. The operations include arithmetic and logic operations. The operating system performs multiple routines for performing a number of tasks required to assign input devices 1107, output devices 1110, for example, the 3D printer 1003, and memory for execution of the image integrator 1002a, the digital simulator 1002b, and the digital modeler 1002c. The tasks performed by the operating system comprise assigning memory to the image integrator 1002a, the digital simulator 1002b, and the digital modeler 1002c and data, moving data between memory 1102 and disk units and handling input/output operations. The operating system performs the tasks on request by the operations and after performing the tasks, the operating system transfers the execution control back to the processor 1101. The processor 1101 continues the execution to obtain one or more outputs. The outputs of the execution of the image integrator 1002a, the digital simulator 1002b, and the digital modeler 1002c are displayed to the user on the display unit 1106.

It will be readily apparent that the various methods and algorithms described herein may be implemented in a computer readable medium appropriately programmed for general purpose computers and computing devices. Typically a processor, for example, one or more microprocessors will receive instructions from a memory or like device, and execute those instructions, thereby performing one or more processes defined by those instructions. Further, programs that implement such methods and algorithms may be stored and transmitted using a variety of media, for example, computer readable media in a number of manners. In one embodiment, hard-wired circuitry or custom hardware may be used in place of, or in combination with, software instructions for implementation of the processes of various embodiments. Thus, embodiments are not limited to any specific combination of hardware and software. A "processor" means any one or more microprocessors, central processing unit (CPU) devices, computing devices, microcontrollers, digital signal processors or like devices. The term "computer readable medium" refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include dynamic random access memory (DRAM), which typically constitutes the main memory. Transmission media include coaxial cables, copper wire and fiber optics, including the wires that comprise a system bus coupled to the processor. Common forms of computer readable media include, for example, a floppy disk, a flexible disk, hard disk, magnetic tape, any other magnetic medium, a compact disc-read only memory (CD-ROM), digital versatile disc (DVD), any other optical medium, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, a carrier wave as described hereinafter, or any other medium from which a computer can read. In general, the computer readable programs may be implemented in any programming language. Some examples of languages that can be used include C, C++, C#, Perl, Python, or JAVA. The software programs may be stored on or in one or more mediums as an object code. A computer program product comprising computer executable instructions embodied in a computer readable medium comprises computer parsable codes for the implementation of the processes of various embodiments.

Where databases are described such as the image database 1002d, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats including relational databases, object-based models and/or distributed databases could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, a local area network (LAN), a wide area network (WAN) or the Ethernet, token ring, or via any appropriate communications means or combination of communications means. Each of the devices may comprise computers, such as those based on the Intel® processors, AMD® processors, UltraSPARC® processors, Sun® processors, IBM® processors, etc. that are adapted to communicate with the computer. Any number and type of machines may be in communication with the computer.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A method for fabricating a dental prosthesis for a patient, comprising:
    acquiring one or more high resolution digital scanned images of one or more oral structures of said patient using one or more digital image scanning devices, wherein said oral one or more structures comprise maxillary and mandibular bone and dentition of said patient;
    acquiring one or more three dimensional cone beam X-ray images of hard oral tissues and soft oral tissues of said patient using a cone beam X-ray image device, wherein said one or more three dimensional cone beam X-ray images of said hard oral tissues and said soft oral tissues comprise the maxillary and mandibular bone and dentition, temporomandibular joint, and upper lip and lower lip;
    integrating said one or more high resolution digital scanned images of said one or more oral structures with said one or more three dimensional cone beam X-ray images of said hard oral tissues and said soft oral tissues of said patient in a three dimensional space to obtain one or more combined three dimensional images of said one or more oral structures of said patient, comprising:
        analyzing three dimensional image data to digitally accomplish a face bow transfer in said three dimensional space with high accuracy based on said one or more high resolution digital scanned images and said one or more three dimensional cone beam X-ray images, wherein said three dimensional image data comprises accurate three dimensional data of upper jaw in relation to a maxilla, lower jaw, and condyle of said patient;
        separating three dimensional image data of the lower jaw from three dimensional image data of the upper jaw, wherein said three dimensional image data of said lower jaw comprise lower teeth and said soft oral tissues in a single group to simulate an independent movement of said lower jaw as a rigid body;
        identifying a plurality of common discrete three dimensional reference data points in said one or more high resolution digital scanned images and said one or more three dimensional cone beam X-ray images, wherein said plurality of common discrete three dimensional reference data points comprise an incisal edge of a same front teeth; and,
        converting each of said three dimensional image data into said three dimensional space based on said plurality of common discrete three dimensional reference data points;
    digitally simulating an occlusal relationship between upper oral structures and lower oral structures using said combined three dimensional images for digitally articulating said upper oral structures and said lower oral structures;
    digitally modeling said dental prosthesis based on said digitally articulated upper oral structures and lower oral structures to generate a digital dental prosthesis model for planning intra-oral positioning and structure of said dental prosthesis;
    refining said digital dental prosthesis model based on simulated force tests performed for assessing interference between different components of said digital dental prosthesis model with each other and with said one or more oral structures of said patient and retention of said digital dental prosthesis model;
    creating a prospective dental prosthesis model based on said refined digital dental prosthesis model, wherein said prospective dental prosthesis model is tested for verifying predetermined functions of said prospective dental prosthesis model; and
    fabricating said dental prosthesis based on said tested and verified prospective dental prosthesis model.

2. The method of claim 1, further comprising subjecting said fabricated dental prosthesis to a milling process comprising:
    acquiring a three dimensional image, spatial location, and orientation of said fabricated dental prosthesis;
    configuring an automated milling sequence based on a comparison between said acquired three dimensional image of said fabricated dental prosthesis and said refined digital dental prosthesis model; and milling said fabricated dental prosthesis based on said milling sequence for gross cutting and fine detailing of said fabricated dental prosthesis.

3. The method of claim 1, wherein said dental prosthesis is one of a removable complete denture dental prosthesis, a removable partial denture dental prosthesis, and a detachable fixed dental prosthesis anchored on one of natural oral structures and implanted oral structures.

4. The method of claim 1, wherein said occlusal relationship between said upper oral structures and said lower oral structures is digitally simulated at different condylar positions for digitally reproducing bite registration, centric occlusion, and centric relation.

5. The method of claim 1, wherein said intra-oral positioning and said structure of said dental prosthesis are planned for achieving optimal occlusion, retention, smile profile, and for meeting phonetic requirements of said dental prosthesis.

6. The method of claim 1, wherein said digitally modeling of said dental prosthesis comprises establishing a preliminary digital model of said dental prosthesis using pre-scanned digital models from an image database of dental prosthesis design, wherein said preliminary digital model of said dental prosthesis is established by matching said pre-scanned digital models with jaw morphology and configuration of said patient obtained by characterizing arch form and size of upper and lower jaws, ridge height and form, and inter-jaw space and relation.

7. The method of claim 6, wherein said preliminary digital model of said dental prosthesis is established by simulating and parameterizing elastic response of said soft oral tissues, occlusion force interaction between upper teeth and lower teeth, condylar guidance, lifting force of upper lip and lower lip, tongue motion, and oral muscles during primary motions of said one or more oral structures of said patient.

8. The method of claim 1, further comprising providing an image database comprising a record of said digital dental prosthesis model and pre-scanned digital models of a plurality of different dental prostheses based on multiple forms of dentition and upper and lower jaw configuration.

9. The method of claim 1, wherein said simulated force tests are performed for reducing interference and enhancing retention of said digital dental prosthesis model by simulating predetermined motions of said one or more oral structures, and wherein refining said digital dental prosthesis model comprises modifying position, alignment and height of teeth of said digital dental prosthesis model.

10. The method of claim 1, further comprising digitally modeling an acrylic base of said dental prosthesis based on said simulated force tests, wherein said acrylic base is configured for establishing a complete peripheral air tight seal with said hard oral tissues and said soft oral tissues to achieve suction based retention of said dental prosthesis.

11. The method of claim 1, wherein said predetermined functions of said prospective dental prosthesis model comprise retention of said prospective dental prosthesis model, esthetics of said prospective dental prosthesis model, and occlusion and phonetics of said prospective dental prosthesis model.

12. The method of claim 1, wherein said combined three dimensional images render low resolution images of upper jaw bones and lower jaw bones, roots of teeth, and temporomandibular joint complex, and high resolution images of coronal portion of said teeth and said soft oral tissues that potentially interface with said dental prosthesis.

13. The method of claim 1, wherein said dental prosthesis is fabricated by one of casting metal into a preformed space of said prospective dental prosthesis model and molding acrylic material into a preformed space of said prospective dental prosthesis model.

14. The method of claim 1, wherein said dental prosthesis is fabricated by rigidly attaching preformed prosthetic teeth to a predesigned abutment on an acrylic base of said dental prosthesis, wherein said base of said dental prosthesis is fabricated by precision milling of preformed blocks of high density and high strength acrylic material, and wherein each of said preformed prosthetic teeth has a shape of a dental crown.

15. The method of claim 1, wherein said testing of said prospective dental prosthesis model comprises analyzing and incorporating modifications into said refined digital dental prosthesis model, creating a modified prospective dental prosthesis model, and verifying said modified prospective dental prosthesis model.

16. The method of claim 1, further comprising modifying base and framework of a prefabricated dental prosthesis for maximizing retention and function of said prefabricated dental prosthesis by adapting said base to said soft oral tissues and providing anchorage with intra-oral dentition.

17. A system for fabricating a dental prosthesis for a patient, comprising:

one or more digital image scanning devices that acquire one or more high resolution digital scanned images of one or more oral structures of said patient;

a cone beam X-ray image device that acquires one or more three dimensional cone beam X-ray images of hard oral tissues and soft oral tissues of said patient;

an image integrator provided on a computing device, wherein said image integrator integrates said one or more high resolution digital scanned images of said one or more oral structures with said one or more three dimensional cone beam X-ray images of said hard oral tissues and said soft oral tissues of said patient in a three dimensional space to obtain one or more combined three dimensional images of said one or more oral structures of said patient;

said image integrator for analyzing three dimensional image data to digitally accomplish a face bow transfer in said three dimensional space with accuracy based on said one or more high resolution digital scanned images and said acquired three dimensional cone beam X-ray images, wherein said three dimensional image data comprises accurate three dimensional data of upper jaw in relation to a maxilla, lower jaw, and condyle of said patient;

said integrator for separating three dimensional image data of the lower jaw from three dimensional image data of the upper jaw, wherein said three dimensional image data of said lower jaw comprise lower teeth and said soft oral tissues in a single group to simulate an independent movement of said lower jaw as a rigid body;

said integrator identifies a plurality of common discrete three dimensional reference data points in said one or more high resolution digital scanned images and said one or more three dimensional cone beam X-ray images, wherein said plurality of common discrete three dimensional reference data points comprise an incisal edge of a same front teeth; and, said integrator converts said one or more high resolution digital scanned images and said one or more three dimensional cone beam X-ray images into said three dimensional space based on said plurality of common discrete three dimensional reference data points;

a digital simulator provided on said computing device, wherein said digital simulator digitally simulates an occlusal relationship between upper oral structures and lower oral structures using said combined three dimensional images for digitally articulating said upper oral structures and said lower oral structures;

a digital modeler provided on said computing device, wherein said digital modeler:
  digitally models said dental prosthesis based on said digitally articulated upper oral structures and lower oral structures to generate a digital dental prosthesis model for planning intra-oral positioning and structure of said dental prosthesis; and
  refines said digital dental prosthesis model based on simulated force tests performed for assessing interference and retention of said digital dental prosthesis model;

a three dimensional printer for creating a prospective dental prosthesis model based on said refined digital dental prosthesis model, wherein said prospective dental prosthesis model is tested for verifying predetermined functions of said prospective dental prosthesis model; and a fabricator that fabricates said dental prosthesis based on said tested and verified prospective dental prosthesis model.

18. The system of claim 17, further comprising an image database comprising pre-scanned digital models of a plurality of different dental prostheses based on multiple forms of dentition and upper and lower jaw configuration.

19. The system of claim 18, wherein said digital modeler establishes a preliminary digital model of said dental prosthesis using said pre-scanned digital models from said image database, wherein said digital modeler establishes said preliminary digital model of said dental prosthesis by matching said pre-scanned digital models with jaw morphology and configuration of said patient by characterizing arch form and size of upper and lower jaws, ridge height and form, and inter-jaw space and relation.

20. The system of claim 17, wherein said digital simulator digitally simulates said occlusal relationship between said upper oral structures and said lower oral structures at different condylar positions for digitally reproducing bite registration, centric occlusion, and centric relation.

21. The system of claim 17, wherein said digital simulator performs said simulated force tests for reducing interference and enhancing retention of said digital dental prosthesis model by simulating predetermined motions of said one or more oral structures.

22. The system of claim 17, wherein said dental prosthesis is one of a removable complete denture dental prosthesis, a removable partial denture dental prosthesis, and a detachable fixed dental prosthesis anchored on one of natural oral structures and implanted oral structures.

23. The system of claim 17, wherein said fabricator fabricates said dental prosthesis by one of casting metal into a preformed space of said prospective dental prosthesis model and molding acrylic material into a preformed space of said prospective dental prosthesis model.

24. The system of claim 17, wherein said fabricator fabricates said dental prosthesis by rigidly attaching preformed prosthetic teeth to a predesigned abutment on an acrylic base of said dental prosthesis, wherein said base of said dental prosthesis is fabricated by precision milling of preformed blocks of high density and high strength acrylic material, and wherein each of said preformed prosthetic teeth has a shape of a dental crown.

25. The system of claim 17, wherein said fabricator fabricates precision-driven removable temporomandibular joint appliances, esthetic appliances, and orthodontic aligners.

26. A non-transitory computer program product comprising computer executable instructions embodied in a computer readable storage medium, wherein said computer program product comprises:

a first computer parsable program code for integrating one or more high resolution digital scanned images of one or more oral structures with one or more three dimensional cone beam X-ray images of hard oral tissues and soft oral tissues of a patient in a three dimensional space to obtain one or more combined three dimensional images of said one or more oral structures of said patient;

a second computer parsable program code for analyzing three dimensional image data to digitally accomplish a face bow transfer in said three dimensional space with high accuracy based on said one or more high resolution digital scanned images and said one or more three dimensional cone beam X-ray images, wherein said three dimensional image data comprises accurate three dimensional data of upper jaw in relation to a maxilla, lower jaw, and condyle of said patient;

a third computer parsable program code for separating three dimensional image data of the lower jaw from three dimensional image data of the upper jaw, wherein said three dimensional image data of said lower jaw comprise lower teeth and said soft oral tissues in a single group to simulate an independent movement of said lower jaw as a rigid body;

a fourth computer parsable program code for identifying a plurality of common discrete three dimensional reference data points in said one or more high resolution digital scanned images and said one or more three dimensional cone beam X-ray images, wherein said plurality of common discrete three dimensional reference data points comprise an incisal edge of a same front teeth;

a fifth computer parsable program code for converting said one or more high resolution digital scanned images and said one or more three dimensional cone beam X-ray images into said three dimensional space based on said plurality of common discrete three dimensional reference data points;

a sixth computer parsable program code for digitally simulating occlusal relationship between upper oral structures and lower oral structures using said combined three dimensional images for digitally articulating said upper oral structures and said lower oral structures;

a seventh computer parsable program code for digitally modeling a dental prosthesis based on said digitally articulated upper oral structures and lower oral structures to generate a digital dental prosthesis model for planning intra-oral positioning and structure of said dental prosthesis; and an eighth computer parsable program code for refining said digital dental prosthesis model based on simulated force tests performed for assessing interference and retention of said digital dental prosthesis model.

* * * * *